United States Patent
Fedder et al.

(10) Patent No.: US 10,608,614 B2
(45) Date of Patent: Mar. 31, 2020

(54) METHOD AND DEVICE FOR BI-STATE CONTROL OF NONLINEAR RESONATORS

(71) Applicant: CARNEGIE MELLON UNIVERSITY, a Pennsylvania Non-Profit Corporation, Pittsburgh, PA (US)

(72) Inventors: Gary K. Fedder, Turtle Creek, PA (US); Congzhong Guo, Santa Clara, CA (US)

(73) Assignee: CARNEGIE MELLON UNIVERSITY, Pittsburgh, PA (US)

(*) Notice: Subject to any disclaimer, the term of this patent is extended or adjusted under 35 U.S.C. 154(b) by 38 days.

(21) Appl. No.: 14/627,801

(22) Filed: Feb. 20, 2015

(65) Prior Publication Data

US 2016/0072472 A1    Mar. 10, 2016

Related U.S. Application Data

(60) Provisional application No. 61/966,280, filed on Feb. 20, 2014.

(51) Int. Cl.
| | |
|---|---|
| *H01L 23/473* | (2006.01) |
| *H02M 1/14* | (2006.01) |
| *H02M 1/34* | (2007.01) |
| *H03J 1/00* | (2006.01) |
| *G01N 29/12* | (2006.01) |
| *G01N 29/036* | (2006.01) |
| *G01L 1/10* | (2006.01) |
| *G01N 29/02* | (2006.01) |
| *G01C 19/5776* | (2012.01) |

(52) U.S. Cl.
CPC ............ *H03J 1/00* (2013.01); *G01L 1/10* (2013.01); *G01N 29/022* (2013.01); *G01N 29/036* (2013.01); *G01N 29/12* (2013.01); *G01C 19/5776* (2013.01); *G01N 2291/0256* (2013.01); *G01N 2291/02491* (2013.01)

(58) Field of Classification Search
CPC ................................ G03B 5/124; G01P 15/097
See application file for complete search history.

(56) References Cited

U.S. PATENT DOCUMENTS

| | | | | |
|---|---|---|---|---|
| 5,442,510 A | * | 8/1995 | Schwartz ............. | G05B 5/01 700/32 |
| 6,497,141 B1 | * | 12/2002 | Turner ............... | H03H 9/2405 310/309 |
| 8,384,372 B1 | * | 2/2013 | Behlow, Jr. ......... | G01N 29/036 324/76.41 |
| 2009/0309613 A1 | * | 12/2009 | Hollocher ........... | B81B 3/0008 324/661 |

(Continued)

OTHER PUBLICATIONS

Guo, Congzhong, et al. "Bi-state control of parametric resonance." Applied Physics Letters 103, No. 18 (2013): 183512.

(Continued)

*Primary Examiner* — Jorge L Carrasquillo
*Assistant Examiner* — Charles S Laughlin
(74) *Attorney, Agent, or Firm* — Michael G. Monyok

(57) ABSTRACT

A bi-state bifurcation-based control system and method for nonlinear resonators, which utilizes a control loop to servo on the edge of the bifurcation jump, either at the maximum "on" point prior to the Duffing bifurcation jump or along the rising edge of the parametric bifurcation.

18 Claims, 10 Drawing Sheets

(56) References Cited

U.S. PATENT DOCUMENTS

2013/0009716 A1* 1/2013 Phan Le ............... H03H 9/2431
331/154
2014/0132186 A1* 5/2014 Tazartes ............. G01C 19/5776
318/128

OTHER PUBLICATIONS

Guo, Congzhong. "Bi-state Control of Microelectromechanical Nonlinear and Parametric Resonance." Disseration, Carnegie Mellon University, Sep. 2013.
Guo, Congzhong, et al. "Bi-state control of a duffing microresonator on the falling edge of the instability." In Solid-State Sensors, Actuators and Microsystems (Transducers & Eurosensors XXVII), 2013 Transducers & Eurosensors XXVII: The 17th International Conference on, pp. 1703-1706. IEEE, 2013.

* cited by examiner

METHOD AND DEVICE FOR BI-STATE CONTROL OF NONLINEAR RESONATORS

CROSS-REFERENCE TO RELATED APPLICATIONS

This application claims the benefit under 35 U.S.C. § 119 of U.S. Provisional Application Ser. No. 61/966,280, filed Feb. 20, 2014, which is incorporated by reference herein in its entirety.

STATEMENT REGARDING FEDERALLY SPONSORED RESEARCH

This invention was made with government support under the National Science Foundation CNS 0941497. The government has certain rights in this invention.

BACKGROUND OF THE INVENTION

The field of the invention relates generally to non-linear resonators. Resonant-based sensing has long been exploited to gauge micromechanical system parameters such as mass and spring constant. Gravimetric sensors and mass flow meters that measure the mass change and the stress sensors that link to suspension spring constant changes all exemplify this approach. As harmonic resonators suffer from a direct link between amplitude and frequency noise that degrades sensitivity, it would be advantageous to use a class of nonlinear parametric resonators for developing an extremely sensitive mechanism to reveal tiny changes in resonance characteristics. This improved sensitivity stems from an instantaneous "jump" transition from near-zero to high displacement in parametric resonators, yielding high ratio of resonant amplitude to the minimum detectable amplitude signal.

The harmonic and parametric resonators differ in the way the resonance is excited. The harmonic resonator has a fixed spring constant, with an external drive that is sinusoidal in time t and invariant in displacement x. The parametric resonator is driven by a nonlinear electrostatic drive at an electrical frequency that creates a displacement-dependent spring constant $k_{eff}$. Parametric resonance conditions are satisfied when the periodic variation of $k_{eff}$ is at twice the natural mechanical resonance frequency or at other integer multiples fraction of twice the natural mechanical resonance frequency (i.e., $2\omega_r/n$, where $\omega_r$ is the natural mechanical resonant frequency and n is an integer larger or equal to 1).

A microelectromechanical parametric resonator operates in two states—one "off" state that has zero motion and the other "on" state whose amplitude increases exponentially over time. In the "off" state, the resonator is nominally perfectly balanced at rest. However, because of the existence of thermomechanical noise or with the existence of external disturbances, a very small but non-zero noise displacement typically on the order of femtometers to nanometers is present, depending on the level of noise inherent in the system. With non-zero displacement and application of a parametric drive voltage under appropriate pump frequencies where the parametric resonance condition is satisfied, the mass-spring-damper system periodically increases (hardens) or decreases (softens) its effective spring force, resulting in the mass being pumped into parametric resonance.

An instantaneous bifurcation "jump" is seen from a near-zero "off" state (point A) to a non-zero high amplitude (point B) "on" state in the representative steady-state amplitude versus frequency characteristic in FIG. 1. This sharp transition from A to B is called "bifurcation". Quality factor (Q), which is inversely related to energy loss per cycle, is an important metric used to evaluate the performance of a resonator. Lower loss generally gives rise to a sharper amplitude peak in the frequency spectrum. The infinitely steep slope on the bifurcation edge effectively enhances Q-factor. This intriguing property promotes many ultra-sensitive sensor applications such as mass flow rate sensors, gravimetric sensors, magnetometers and strain sensors, and is used in noise-squeezing applications for parametric amplification.

An analogous bifurcation response occurs in a micromechanical Duffing resonator, where the bending of the resonance amplitude curve is due to the mechanical nonlinearity. The bending leads to multi-valued solutions for one particular frequency, which results in "bi-stability" in frequency response.

To enable parametric resonance and/or Duffing resonance to be used in making an ultra-sensitive mass sensor or strain gauge, a drive scheme is needed to excite the parametric resonance and control the servo such that the controlled setpoint along the bifurcation "jump" is maintained. Bifurcation-based control approach can be realized both open-loop and closed-loop. The former is slow, sometimes taking up to minutes since the parametric drive frequency is swept with fine increments until a jump in amplitude is observed, and is impractical for most practical (real-time) sensing applications. The closed-loop scheme in principle can servo along the jump point (for example, the point along A-B in FIG. 1) enabling rapid readout of the bifurcation amplitude and/or frequency. There are two practical limits to this approach. One is due to the hysteresis (jumps can occur at A-B or S-P depending on the direction of the frequency sweep), which inhibits the amplitude from readily moving back to its original state once the amplitude has transitioned across the bifurcation. The other limitation originates from a slow-time manifold that the resonator state has to travel in order to transit between "on" and "off" states. This slow-time manifold on the system trajectory is relatively long (on the order of seconds), inhibiting stable servo operation when linear feedback control approaches are applied.

One analog bifurcation control approach takes the phase variance as the input of the controller. These controllers are generally complex and difficult for on-chip implementation. It also produces a relatively small amplitude on the order of 100 pm. The advantage of the controller of the present invention is its practical feasibility for on-chip circuit implementation and its ability to servo at relatively large amplitude (typically about four orders of magnitude larger in the displacement amplitude than the 100 pm amplitude) along the sharp jump of the bifurcation without altering the plant.

BRIEF SUMMARY OF THE INVENTION

According to one embodiment of the present invention, a bi-state bifurcation-based control system comprising a resonator 100 and a controller 301 is described that is useful for ultrasensitive micro-electromechanical systems (MEMS) applications and addresses issues of hysteresis and long settling time. One key aspect of this invention is the use of a bi-state switching that is set to a speed much faster than the amplitude response dynamics of the resonator 100. Switching is accomplished by modulating the spring constant of the parametric resonator 100 using two distinct drive voltage levels and a pulse width modulator 302 to control alternating between each drive voltage level. The servo setpoint 500 is chosen along the sharp jump transition, i.e., along the line between A and B or between S and P as indicated in FIG. 1. The two dots are two possible setpoints 500; a multitude of different setpoints 500 along the bifurcation lines A-B and S-P could be chosen. However, only one setpoint 500 is controlled by a corresponding bi-state control system at a given time.

In one embodiment, a parametric resonator 100 is driven by a DC parametric drive voltage, $V_{dc}$, in series with an AC excitation voltage, $V_{ac}$. The principle of this control technique is to fix the frequency and amplitude of $V_{ac}$ such that the system is driven into either the "on" or "off" state with the appropriate corresponding value of $V_{dc}$. In this embodiment, $V_{ac}$ is a sinusoidal signal. However the signal could be a square wave, a triangle wave, or any other periodic waveform that has a fundamental component at the appropriate frequency. The DC bias voltage is controlled by the feedback and constrained to take one of the two values in a pulse modulation scheme. In this case, the pulse width modulation voltage, $\upsilon_{PWM}$, effectively takes on the role of $V_{dc}$ but having two distinct DC values. The constraint that the parametric drive amplitude $\upsilon_{PWM}$ is only allowed to take one of the two possible values (one in the "on" region, and the other in the "off" region) highlights the key feature of this control scheme. In the embodiment shown in FIG. 2, the feedback pulse frequency is fixed and the duty cycle is modulated (i.e., pulse width modulation is employed). In addition to addressing the issues of limit cycling and instability, this approach also achieves a high ratio of resonant amplitude to the minimum detectable amplitude signal with much higher controlled amplitude.

In an alternative embodiment, shown in FIG. 6, the control system states for a Duffing microresonator 100 are set through bi-state amplitude modulation of the AC drive gain $V_{ac}$ while operating at a fixed drive frequency such that one of the system states is within an "instability tongue" whereas the second state resides outside of this tongue, shown in FIG. 5. The tongue draws the boundary between the high displacement and low displacement regions. The DC drive voltage and the frequency are fixed. In the representative example shown in FIG. 4, the amplitude servo point B is chosen at the maximum "on" amplitude prior to the bifurcation jump event.

DETAILED DESCRIPTION OF THE INVENTION

Figure 1:
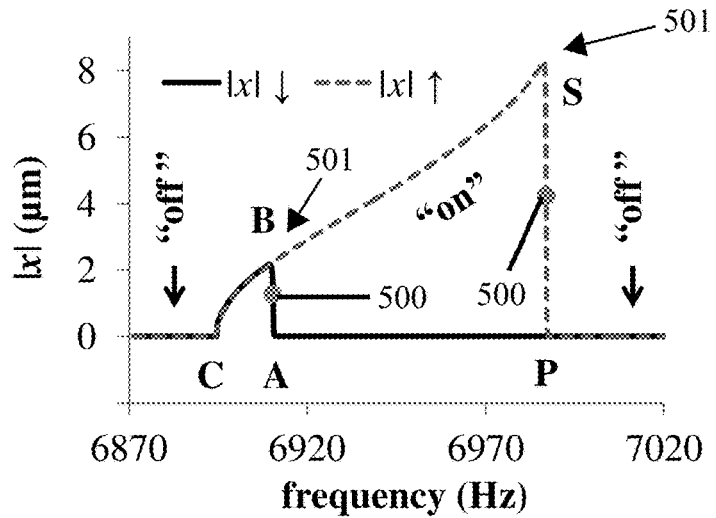
FIG. 1 is a chart illustrating steady-state frequency response of a nonlinear parametric resonator.
Figure 4:
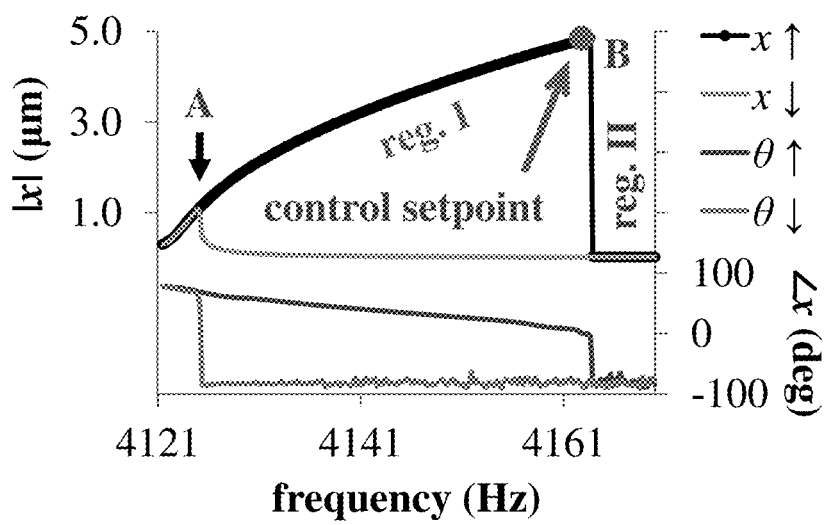
FIG. 4 is a chart illustrating hysteresis of a Duffing resonator, indicating point A as the down-sweep bifurcation frequency and point B as a control point that is just below the up-sweep bifurcation frequency.

A control system and method of the present invention makes possible the highly sensitive detection of mass or strain change by utilizing the bifurcation behavior inherent in a class of nonlinear parametric resonators 100 and in Duffing resonators 100. As shown in FIG. 1 and FIG. 4, the bifurcation behavior is represented as sharp increase in amplitude during a frequency sweep. Depending on the direction of travel of the frequency sweep, the bifurcation jump 501 occurs along the lower frequency transition or higher frequency transition.

Figure 2:
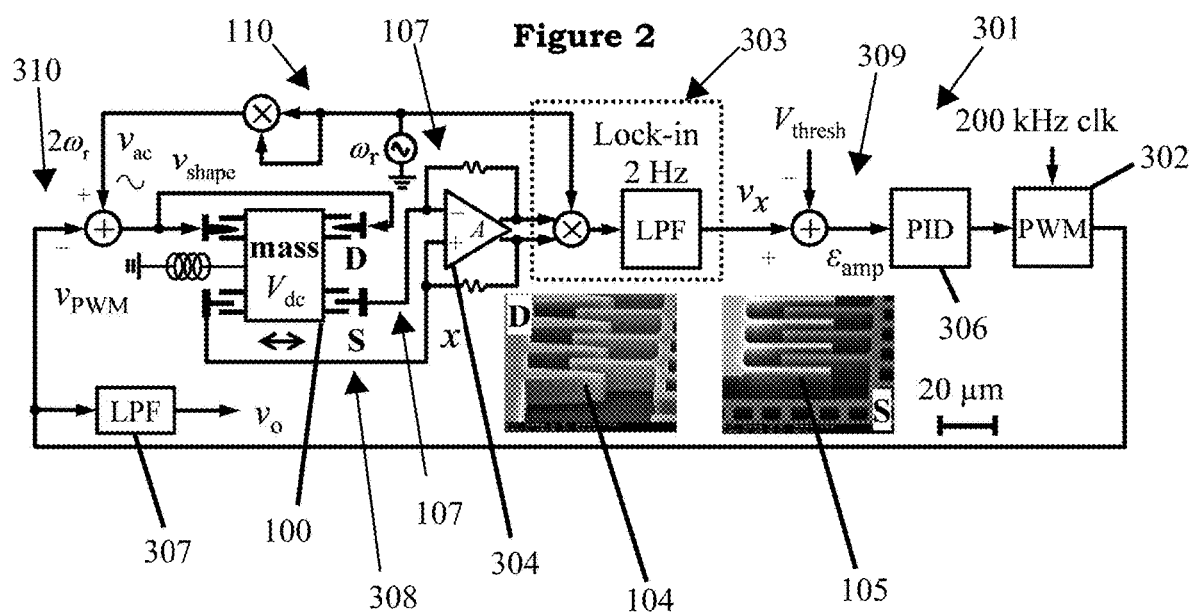
FIG. 2 is the block diagram of the of the bi-state control system, according to one embodiment, with a Silicon-On-Insulator (SOI) MEMS parametric resonator as the plant, together with scanning electron microscope (SEM) views of the parametric drive fingers (D) and capacitive sense fingers (S) (shown as insets).

FIG. 2 illustrates a block diagram of the bi-state bifurcation control system to serve as a general description of the resonator 100 and control loop 301 and is described in detail in the embodiments below. As shown in FIG. 2, the system is comprised of a parametric resonator 100 having capacitive drive combs 104 and capacitive sense combs 105. A direct current (DC) drive voltage is applied across the drive combs 104 to set the effective spring constant of the resonator 100. The sense combs 105 provide information used in a control loop 301 that switches the resonator 100 between "on" and "off" states. The combs 104 and 105 are comprised of a primary set of comb fingers 109 attached to the mass 102 and a corresponding set of fingers 108 that are mechanically anchored. The system further comprises a control loop 301, which may include a drive circuit 310. In one embodiment, the controller, or control loop, 301 further comprises a feedback circuit 308 and an error circuit 309.

Figure 16:
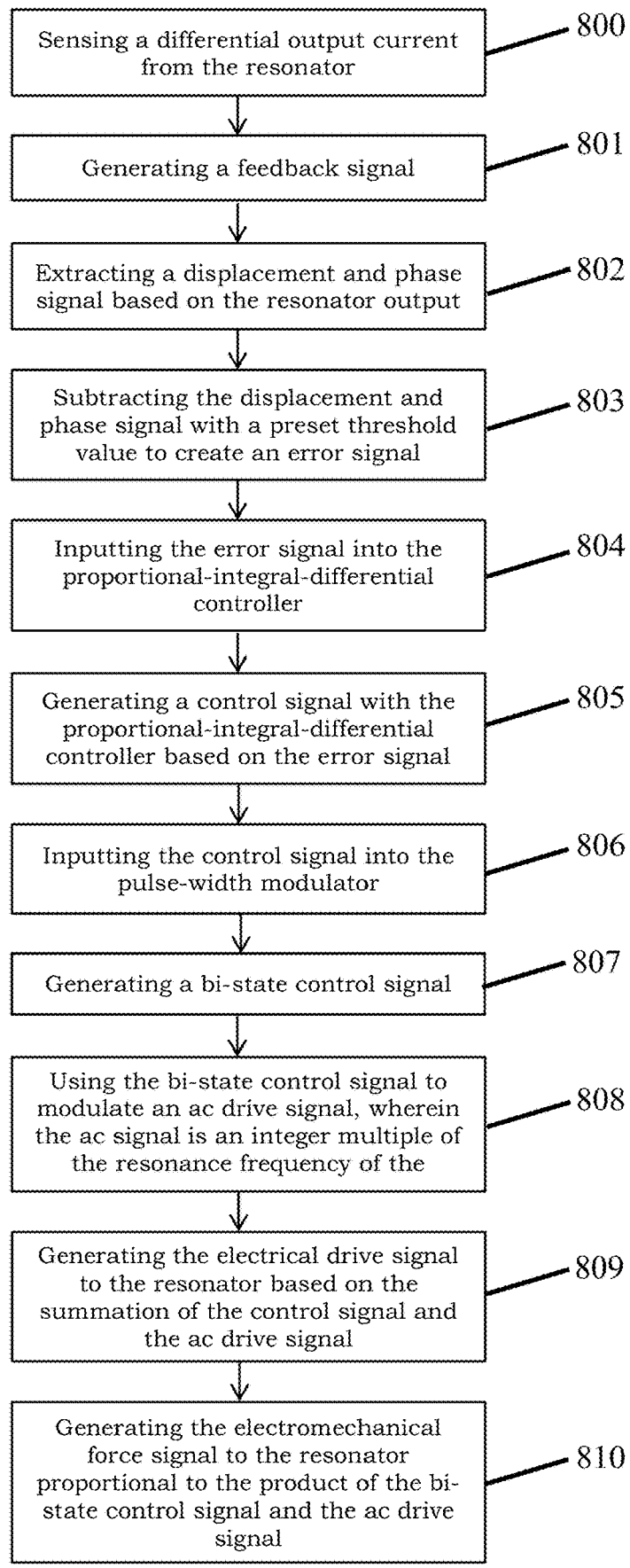
FIG. 16 is a flow diagram of the method of one embodiment of the present invention.

As shown in FIG. 16, the method of control of the resonator 100 according to one embodiment is: at step 800, sensing a differential motional output current from the sense capacitors 105 of a MEMS parametric resonator 100; at step 801, generating a feedback signal; at step 802, extracting displacement and phase signal based on the resonator 100 output (in this embodiment using a lock-in amplifier 303 with a low-pass filter 307 (LPF) having a 2 Hz cutoff frequency); at step 803, subtracting the displacement signal, $\upsilon_x$, with a pre-set threshold, $V_{thresh}$, and generating an error signal, $\varepsilon_{amp}$; at step 804, inputting the error signal into the proportional-integral-derivative controller; at step 805, generating the control signal with the proportional-integral-differential (PID) controller 306 based on the error signal; at step 806, inputting the control signal into the pulse-width-modulator (PWM) 302; at step 807, generating the pulse-width modulated bi-state control signal, $\upsilon_{PWM}$, using the pulse-width modulation module 302; at step 808, using the bi-state control signal to modulate an AC drive signal, $\upsilon_{ac}$, wherein the AC drive signal is at twice the mechanical resonance frequency, $\omega_r$, of the resonator 100; at step 809, generating the electrical drive signal to the resonator 100 based on the summation of the pulse-width modulated bi-state control signal, $\upsilon_{PWM}$, and the AC drive signal, $\upsilon_{ac}$; and at step 810, generating the electromechanical force signal to the resonator 100 proportional to the product of the bi-state control signal and the AC drive signal.

In one embodiment, a parametric control scheme is used to control a MEMS resonator 100 operating under nonlinear parametric resonance conditions. The parametric control scheme addresses the issue of the slow time manifold by servoing along this manifold with a bi-state PWM switching that is set to a speed much faster than the amplitude response dynamics of the resonator 100. In the embodiment shown in FIG. 2, the PWM switching speed is set to 200 kHz. However, other switching speeds can be used as long as the speed is faster than the resonator 100 system dynamics. The servo point 500 is chosen to take a non-zero displacement amplitude (1.9 µm, shown as point C in FIG. 10) that is slightly smaller than the maximum "on" amplitude (2.2 µm). The large displacement servo gives rise to a much higher ratio of signal to noise compared to the current state-of-the-art, which uses a servo point near zero amplitude (e.g., 100 pm). The servo point 500 lies along the bifurcation jump 501 A-B in FIG. 1. The servo point 500 can be set along the bifurcation jump point 501 S-P in FIG. 1, in an alternate embodiment.

In the preferred embodiment, the control plant 101 is a parametric resonator 100 made in a Silicon-On-Insulator (SOI)-MEMS fabrication process with a 15 µm-thick structural silicon device layer forming a micromechanical mass-spring system. Two primary sets of electrostatic comb fingers 109 are attached to the plate mass 102. Corresponding sets of comb fingers 108 are interdigitated with the primary set of comb fingers 109 attached to the mass 102 to form a drive comb 104 and a sense comb 105. The electrostatic sense fingers 109 which forms part of the sense comb 105 (a scanning electron microscope (SEM) image shown in FIG. 2, inset S) have straight sidewalls and act as capacitors whose capacitance varies linearly with displacement. The electrostatic drive comb fingers 109 which form part of the drive comb 104 (a SEM image shown in FIG. 2, inset D) is specially shaped along its sidewalls (for example, non-straight sidewalls) to create a voltage controlled linear spring constant $\gamma_1$ in the force, $F_p$, acting on the resonator 100 in Eq. (1) that is necessary to excite the parametric resonance. A cubic-term spring constant $\gamma_3$ in Eq. (1) provides specific nonlinear behavior that limits the parametric resonance amplitude. The specific effective system nonlinearity can be either hardening (i.e., $\gamma_3 > 0$) or softening (i.e., $\gamma_3 < 0$), which is determined by the combined mechanical and electrostatic nonlinearity. The exemplary embodiment of the control plant 102 in FIG. 2 has a hardening nonlinearity. The bi-state control principle applies to both hardening and softening nonlinear resonators.

$$F_p(t,x) = -(\gamma_1 x + \gamma_3 x^3)[|v_{dc}|^2 + |v_{ac}|^2 \cos(\omega_e t)] \quad (1).$$

In one example of a preferred embodiment, a DC bias voltage $V_{dc,set}$ is applied to a total of 278 moving straight fingers 109 that are attached to a mass 102 of 9 µg. However, any number of fingers 108 and 109 can be used with sensitivity of the system increasing as the number of fingers 108 and 109 increases. As previously stated, the DC bias voltage sets the effective spring constant of the resonator 100. A voltage $\upsilon_{shape}$ formed by summing the DC voltage from the PWM 302, $\upsilon_{PWM}$, with an AC excitation voltage amplitude, $V_{ac}$, is applied on the shaped fingers 108 that are mechanically anchored. The other side of the comb 104, i.e. the fingers 109 attached to the moving plate mass 102, is connected to a fixed DC polarization voltage $V_{dc}$. Capacitive sensing circuits 107 use the set of linear capacitive comb fingers 105, with capacitance $C_s$, and a pair of transimpedance amplifiers 304 (TIA) to measure the differential motional current, $i_x = V_{dc} dC_s/dt$ and subsequently the velocity amplitude, |x|, and phase of the moving mass 102.

Figure 11A:
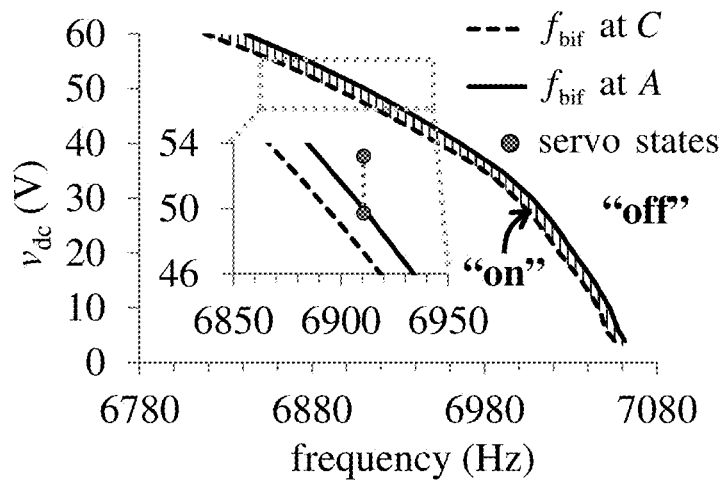
FIG. 11A illustrates the measured bifurcation diagram of the "on" (shaded) and "off" regions for a parametric resonator. Callout shows two servo states that are marked as circles.
Figure 11B:
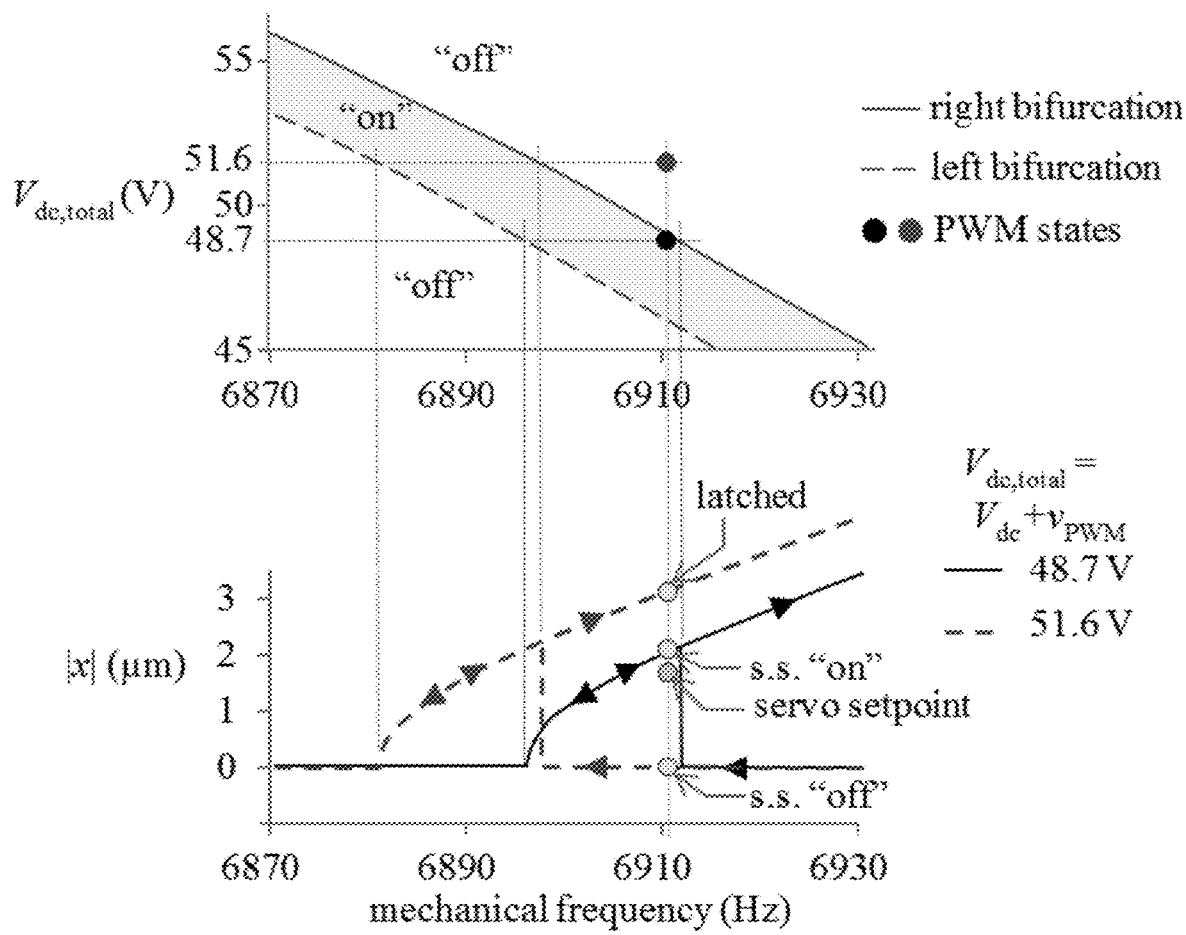
FIG. 11B is a composite view that shows the relationship between the measured bifurcation of a parametric resonator and the corresponding frequency swept resonant amplitudes and that indicates the location of possible operating points at a select drive frequency.

Adjusting the total DC parametric polarization voltage that is applied on the resonator 100 $V_{dc,total} = V_{dc} + \upsilon_{PWM}$ shifts the entire frequency response curve in FIG. 1 and as a result, shifts the bifurcation frequency. This effect is illustrated in FIG. 11 linking the bifurcation frequency to the DC parametric polarization voltage $V_{dc,total}$. With $V_{dc,total}$ varying from 0 to 60 V, solid and dash lines correspond to the "pitch-fork" bifurcation frequencies at points A and C in FIG. 1, respectively. Increasing $V_{dc,total}$ by adjusting the instantaneous value of $\upsilon_{PWM}$, which is controlled by the feedback loop, shifts the frequency response curve (solid curve in FIG. 1) to the left and decreases the bifurcation jump 501 frequency. The specific correlation of the bifurcation frequency characteristic and the resulting frequency response curves is shown in FIG. 11B. The two PWM states shift the bifurcation points in the frequency response curve between "on" and "off" states when driven at the fixed AC drive frequency.

In both embodiments, the DC parametric polarization voltage $V_{dc,total}$ takes two values, one value that drives the device into parametric resonance, and the other value drives the resonator to zero displacement. The bi-state control is accomplished by fixing the parametric drive frequency and the AC drive amplitude $V_{ac}$, such that the system can be readily moved between "on" and "off" states with appropriate value of $V_{dc,total}$ (circles in FIG. 11B). The constraint that the parametric polarization voltage is only allowed to take one of the two possible values (one in the "on" region, and the other in the "off" region) highlights a key characteristic of this control scheme. In contrast, a linear control scheme having a continuum of polarization voltage levels between the two state values would result in an unstable controller and would not servo on the desired setpoint. Instead, such a control system would latch into one of the "latched", steady-state on (s.s. on in FIG. 11B) or steady-state off (s.s. off in FIG. 11B) positions and thus would not track the bifurcation as an average of the PWM 302 output.

Figure 10:
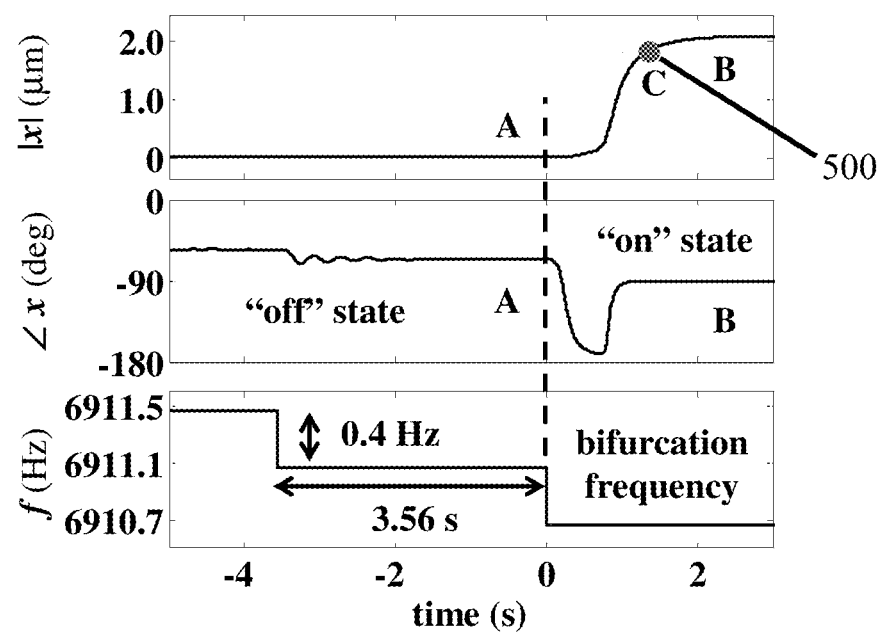
FIG. 10 is the zoom-in view of the frequency down sweep of a parametric resonator in the time domain, where the system state has to travel through the slow time manifold from "off" state (point A) to reach the "on" state (point B).
Figure 12:
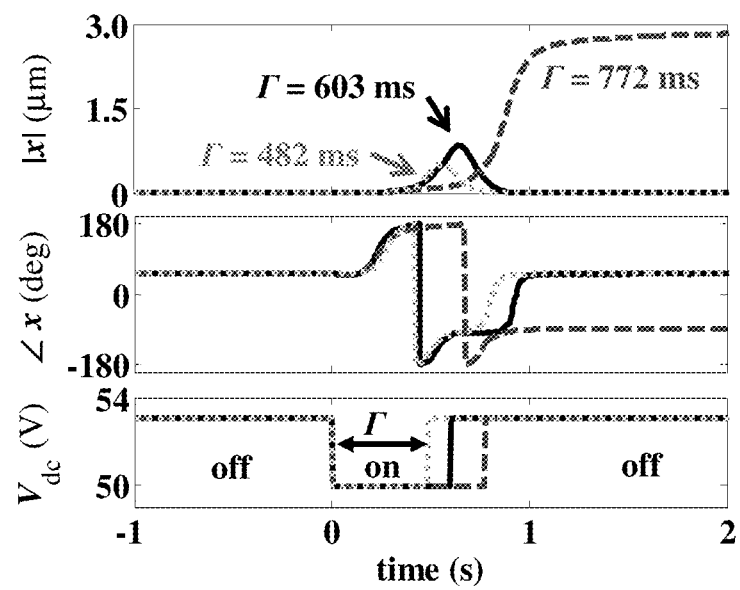
FIG. 12 is a series of charts demonstrating the recapturing of the parametric resonance "zero-vicinity" state.

To illustrate the control dynamics, a first DC parametric polarization voltage $V_{dc,total} = 49.7$ V lands inside the "on"

region, starting to move the state along the slow time manifold in FIG. 10 from point A to B. Before the state completely settles to point B, a second DC parametric polarization voltage $V_{dc,total}$=53.2 V is applied which resides in the "off" region, moving the state back from point B to A. This "recapture" dynamics is shown in FIG. 12. The successful recapturing of the resonator 100 state is guaranteed provided that the "on-state" time Γ is kept shorter than 602.8 ms, in this particular example. The recapturing breaks down if the on-state time is set beyond this critical time. Referring again to FIG. 12, recapturing occurs by rapidly switching back to the "off" state through the use of the control loop 301, with the pulse width modulator 302 alternating the DC voltage based on a set clock speed, as illustrated in FIG. 2.

In a practical control loop 301 that servos on large amplitude, when backing off from B to A, before reaching point A, $V_{dc,total}$ is switched back to the "on" state again, inhibiting the "latch-off", i.e., the displacement reduces to zero. The imposition of the bi-state parametric polarization voltages within the control loop 301 sets the servo point 500 at C in FIG. 10 with an appropriate switching speed (in the example device, an external signal source generates the 200 kHz clock signal) that is much faster than the slow sinusoidal-amplitude system dynamics (typically on the order of 0.5 Hz). Higher switching speeds are possible with appropriately fast electronics and slower switching speeds are possible with a trade-off of increased ripple in the servo amplitude. If the switching speed approaches the slow sinusoidal-amplitude system dynamics, the amplitude will latch states and not servo on the setpoint.

Referring again to FIG. 2, the physical implementation of the bi-state control scheme is schematically shown as a block diagram. A shaped-finger comb parametric resonator 100 serves as the control plant 101. A 3.3 V parametric AC drive voltage amplitude at $2\omega_r$ ($\omega_r$=6910.7 Hz) is generated by an external frequency doubler circuit 110. With appropriate values of $\upsilon_{dc}$, this twice resonance frequency component drives the oscillator into parametric resonance. The amplitude and the phase of the velocity signal $\upsilon_x$, picked off by the TIA 304, are measured by a lock-in amplifier (LIA) 303 which utilizes the signal at $\omega_r$ to demodulate the oscillation velocity signal at resonance. The velocity amplitude output (27.1 mV, as an example) is compared with a preset threshold $V_{thresh}$=25 mV to get the error signal $\varepsilon_{amp}$. This error signal is fed into a proportional-integral-derivative (PID) controller 306 that provides the duty cycle information to the pulse-width-modulation (PWM) module 302. The PWM 302 generates a square waveform with a fixed frequency at 200 kHz, outputting either high or low voltages that correspond to the first DC voltage or the second DC voltage. The PID 306 coefficients are chosen in such a way that the width ratio of the "on" and "off" states is changed to maintain the servo point between the maximum "on" and zero "off" states. This example shows the servo 500 at point C in FIG. 10 with 1.9 μm amplitude to yield a large ratio of servo amplitude to the minimum detectable amplitude. The overall parametric drive voltage across the drive comb fingers 104 is set by the PWM signal $\upsilon_{PWM}$, the AC drive $\upsilon_{ac}$, and the DC bias voltage $V_{dc}$ on the mass 102.

$$\upsilon_{parametric}=|V_{dc}-\upsilon_{ac}+\upsilon_{pwm}| \quad (2).$$

The duty cycle signal is an ultra-sensitive indicator of the servo setpoint 500 along the slow sinusoidal-amplitude dynamics, therefore it is chosen as the controller output $\upsilon_o$, derived by sending the PWM signal through a low pass filter (LPF) 307. The key characteristic of this design ensures that the system is servoing on the slow time manifold by moving between the zero "off" and non-zero "on" regions using the PWM fine-grained control.

Figure 13:
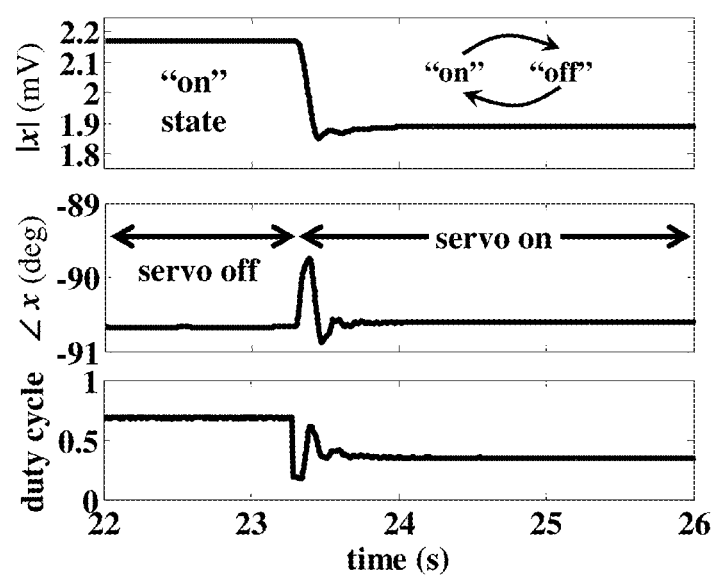
FIG. 13 illustrates the turn-on transient of the bi-state control loop for the parametric control embodiment.

Turn-on dynamics of this bi-state control loop in a vacuum of 18 mTorr, by way of one particular example, is shown in FIG. 13. At 12.8 s, a step change in the parametric drive frequency turns the resonator 100 to the "on" state (2.2 μm) from the "off" state. The controller 301 is turned on at 23.3 s by enabling the PID controller 306. The exemplary proportional and derivative controller 306 coefficients are $k_p$=−141 V/V and $k_d$=−7.1 V-s/V, respectively in this example. The servo point 500 (1.9 μm) backs off from the maximum "on" and settles on the slow time manifold. The duty cycle rings between 0.69 to 0.2 as the servo turns on and then settles to a steady-state control value of around 0.34.

Figure 14:
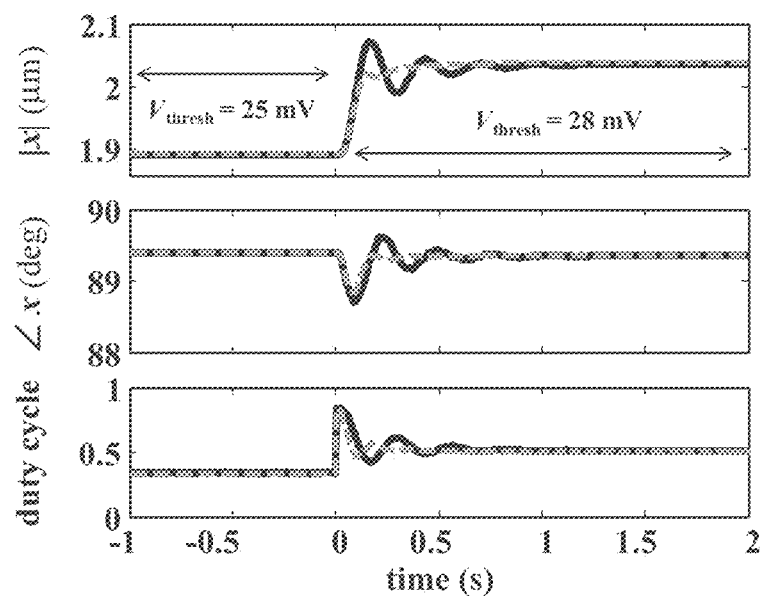
FIG. 14 illustrates shifts in the servo setpoint for a parametric resonator illustrating closed-loop dynamics. Solid curves are obtained with only proportional control and the dash curves are obtained using proportional-derivative control.

Closed-loop dynamics shown in FIG. 14 illustrate the effect of the derivative controller coefficient on the closed-loop dynamics. The servo threshold, $V_{thresh}$, is changed at 0 s from 25 mV (equivalent to 1.75 μm in displacement amplitude |x|) to 28 mV (1.97 μm). With $k_p$=−141 V/V and $k_d$=0, the displacement amplitude changes from 1.89 μm to 2.04 μm with a significant amount of ringing (solid line). This ringing is alleviated by introducing a derivative control coefficient, $k_d$=−7.1 V-s/V, which results in a near critically damped response (dashed line).

The bi-state control scheme for parametric resonators 100 is general and applies to any bi-state feedback scheme, of which the highlighted PWM scheme is a good example. Other possible feedback schemes include pulse-density modulation, for example in delta modulator or delta-sigma modulator architectures. Potentially, other discrete multi-state control schemes could also be employed instead of simply two states in feedback. An example would be in pulse amplitude modulation with a finite number of states. The preceding list is not meant to be exhaustive as many other digital and discrete-amplitude feedback methods exist.

Figure 3:
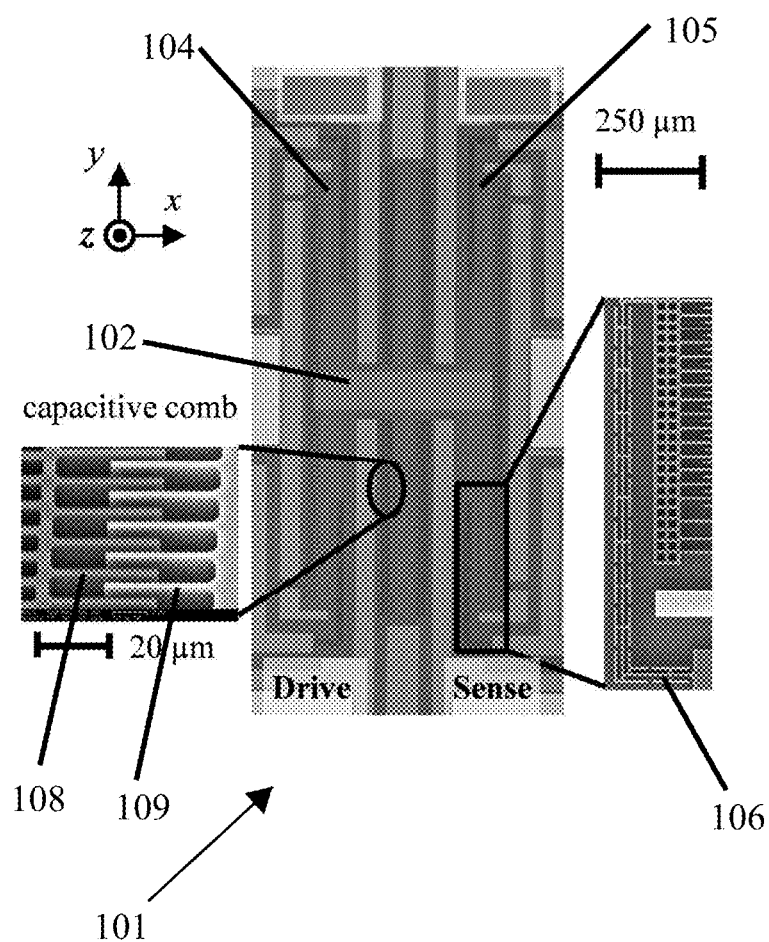
FIG. 3 is an optical microscope image of a microresonator with zoomed-in SEM views of a drive comb and a crab-leg spring.

In another embodiment, the system is a bi-state control system capable of servoing on the falling edge of the microelectromechanical Duffing resonant bifurcation setpoint. As shown in FIG. 3, the system is presented with a 15 μm-thick SOI-MEMS Duffing resonator 100 as the control plant 101, which is comprised of a shuttle mass 102 and a set of capacitive comb fingers 109. Further shown in FIG. 3 is a perspective view of the lateral capacitive combs 104 and 105 electrode geometry of the control plant 101. The capacitive combs 104 and 105 are symmetrically placed on both sides of the shuttle mass 102; the left set serves as the drive electrode 104 and the right set serves as the capacitive pick-off sense electrode 105. The perforated shuttle mass 102 is suspended by four symmetric crab-leg springs, or spring suspension, 106. The nonlinearity inherent in the system stems from the suspension and the nonlinear electrostatic spring constants arising from the comb drive geometry.

The typical measured frequency response of a Duffing resonator 100 is plotted in FIG. 4. Referring to FIG. 4, ↑ symbolizes the frequency up-sweep and ↓ is the frequency down-sweep. This class of nonlinear resonator 100 exhibits a hysteresis effect when the frequency is swept bi-directionally. In the example depicted in FIG. 4, the voltage on the moving shuttle mass 102 is $V_{dc,set}$=10 V and is called the "polarization" voltage. The magnitude of the AC sinusoidal drive on the lateral capacitive comb rotor is $V_{ac}$=25 mV. In this embodiment, the numbers depicted in FIG. 4 correspond to a test performed in a low-pressure environment of 25 mTorr to serve as an illustrative example.

Unlike the linear harmonic resonator, the resonance peak bends toward higher frequencies, yielding multi-valued solutions for any particular frequency value located around the resonance. For example, on the edge of the bent peak at the maximum amplitude (point B on FIG. 4), a jump in the resonance amplitude from 4.8 μm to 0 μm occurs if the drive frequency is increased an infinitesimal amount. The frequency at which the instantaneous jump occurs is called the "bifurcation frequency" $f_B$, which equals 4167 Hz for the setpoint B in FIG. 4. However, the bifurcation frequency can vary depending on the design of the resonator. For a reverse frequency sweep, the jump 501 happens at a lower frequency from 0 μm to 1.0 μm (point A), indicative of a hysteresis effect. The region I between points A and B defines the region where a high amplitude response occurs in response to a frequency change. To the right of point B (region II), the resonance amplitude reduces to very low displacement.

The states for a bi-state control loop can be defined by adjusting the AC drive voltage $V_{ac}$ which shifts the entire frequency response curve in FIG. 4, thus resulting in changes in the bifurcation points A and B. These shifts in A and B are graphically represented in FIG. 5, which defines the "instability tongue" with the locus of the amplitude jump points. The right curve is the up-sweep bifurcation frequency (analogous to point B in FIG. 4) showing the falling edge of the instability; the left curve is the down-sweep bifurcation frequency (point A). The DC polarization voltage is fixed at 10 V in the example loci in FIG. 5.

The changes in the drive voltages modify the system's effective spring constant, which affects the bending of the resonance curve and the regions where the system enters instability. In a typical nonlinear resonator, the drive voltage shapes the instability tongue. The tongue width measured in units of frequency (e.g., Hertz) depends on the AC drive amplitude. The position of the tongue along the frequency axis is a strong function of the DC polarization voltage.

Figure 5:
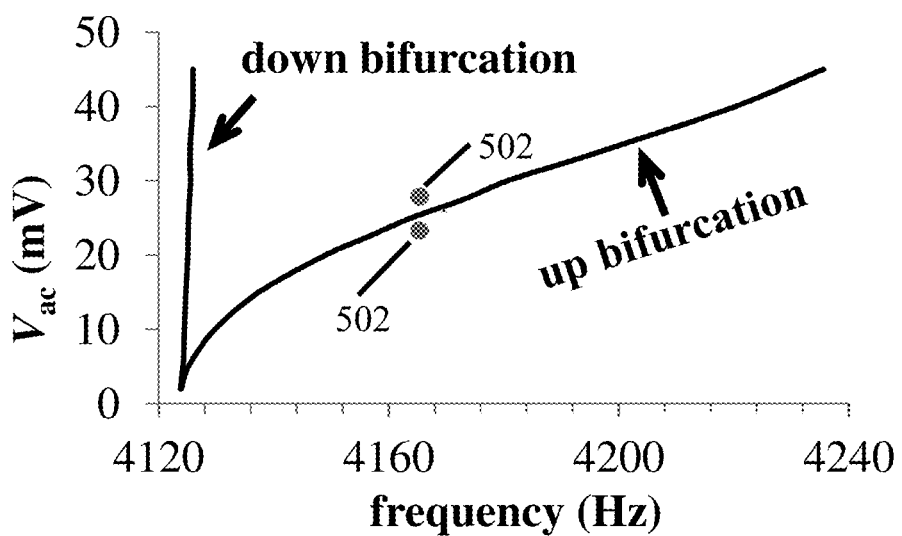
FIG. 5 is a bifurcation diagram of the Duffing resonator showing the locus of the up and down bifurcation points, and the states for the control, where one is located in the high displacement region and the other in the low displacement region.

The points 502 in FIG. 5 identify the states for a bi-state control loop. One of the states ("on" state) is inside the "tongue" that has a large amplitude response; the other state ("off" state) resides outside the "tongue" representing a low amplitude response. The two states center around $V_{ac}$=25 mV and have the same fixed frequency at the bifurcation frequency $f_B$ for the $V_{ac}$=25 mV setpoint. The two states are on opposite sides of the bifurcation point in steady-state operation. Adjusting the AC voltage, $V_{ac}$, near the boundary can move the control state between high and low displacement values. The rapid switching between these two states determines the servo setpoint.

Figure 6:
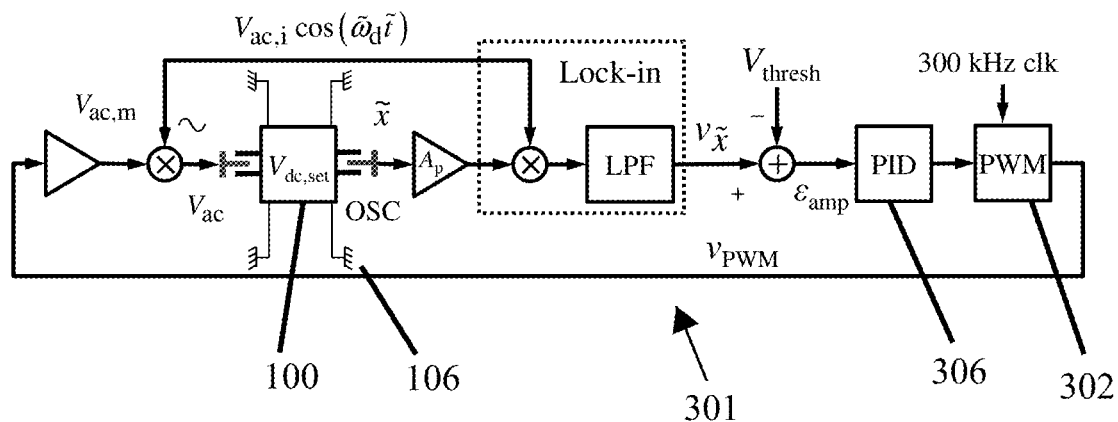
FIG. 6 is the block diagram of a bi-state Duffing resonator control system according to one embodiment.

The control loop 301 is schematically shown in FIG. 6. The control setpoint 500 of the loop 301 is chosen at point B in FIG. 4. The AC drive frequency and the DC bias are fixed to values such that the system can be moved between high and low displacement regions with appropriate bi-state values of AC amplitude $|V_{ac}|$. In one particular example, the DC polarization voltage $V_{dc,set}$=10 V and the AC drive frequency is $f_B$=4167 Hz. The Duffing resonator 100 is driven by $V_{ac}$ whose amplitude and frequency are set by the pulse-width-modulator (PWM) 302 output and the lock-in amplifier (LIA) 303, respectively. A transimpedance amplifier 304 followed by the LIA 303 picks up the resonator velocity amplitude $|v_{\dot{x}}|$. The loop 301 tracks $|v_{\dot{x}}|$ to a fixed setpoint ($V_{thresh}$). The error output is fed into a PID (proportional-integral-derivative) controller 306 to generate the input signal to the PWM 302 representing the pulse-train duty cycle. The output of the PWM 302 generates the bi-state control signal that sets the AC drive amplitude.

The $V_{ac}$ is controlled by the duty-cycle feedback and rapidly adjusts the oscillation between the two states (e.g., high and low displacements) at an example PWM rate of 300 kHz to achieve the servo at the maximum displacement value without turning off the resonator 100. This avoids the long ring-down transient needed to settle from the high displacement state to the low displacement state. This resettling time is inversely proportional to the damping and is typically on the order of 1 s for the resonator 100 operated under a similar vacuum level.

Higher PWM 302 switching rates are possible with appropriately fast electronics and slower switching speeds are possible with a trade-off of increased ripple in the servo amplitude. If the switching speed approaches the slow amplitude Duffing system dynamics (proportional to $2Q/\omega_r$, where Q is the quality factor and $\omega_r$ is the resonant frequency), the amplitude will latch to the zero state and not servo on the high displacement setpoint.

Figure 7:
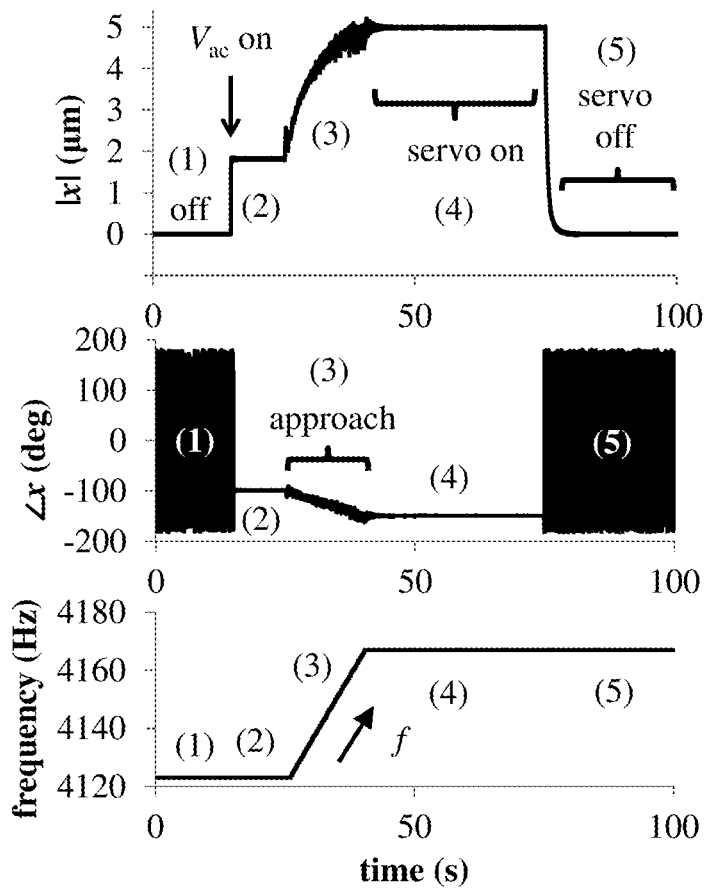
FIG. 7 depicts charts of the turn-on transient of the bi-state control loop for a Duffing resonator.

FIG. 7 shows a series of graphs which depict the turn-on transient of the closed-loop controller 301 with an initial approaching phase. In FIG. 7, the drive AC voltage is turned on at 15 s, followed by an approach phase when the frequency is increased from 4123 Hz to 4167 Hz. The controller 301 is turned on afterwards. At 75 s, the controller 301 is turned off by switching off $V_{ac}$. During region (1), the resonator is off. During region (2), a sinusoidal voltage at 4123 Hz is applied to the resonator 100 drive fingers of comb 104, resulting in a step turn on of the displacement amplitude to a non-zero value due to the capacitive feedthrough. The choice of the initial frequency ensures the resonator 100 is within its low displacement state (to the left of point A in FIG. 4). Region (3) is the necessary "approach" stage when the resonator 100 is turned on to the maximum displacement operation point (point B in FIG. 4) by increasing the drive frequency from 4123 Hz to 4167 Hz. The PID controller 306 threshold $V_{thresh}$ 305 is set in region (4) after reaching this maximum operation point, turning on the servo, after which time the PWM 302 output rapidly changes between 0.3 V and 3.4 V, with duty cycle centered on 0.5. At region (5), the servo is switched off by turning off $V_{ac}$. The phase is well-defined during the time the controller 301 is on and loses track of the input $V_{ac}$ when the controller 301 is turned off. A detailed analysis of the dynamics on the edge of the bifurcation jump 501 provides information on how fast the controller 301 should switch between two states to guarantee successful recapturing of the "on" state. These "off-state" dynamics are characterized in FIG. 8 and FIG. 9.

In open-loop operation, a step change in $V_{ac}$ is introduced from 25.6 mV to 24.1 mV, at which voltage the resonator 100 is not fully in the off state but rather just starting to turn off. $V_{ac}$ is then turned back to 25.6 mV after a prescribed amount of time Γ. When Γ is less than 394.6 ms, the Duffing resonance is successfully recaptured as presented in FIG. 8. When Γ is larger than 395.0 ms, the resonance falls back to the low displacement state. The critical off-state time Γ at which the resonance is on the edge of being recaptured is 394.6 ms.

Figure 8:
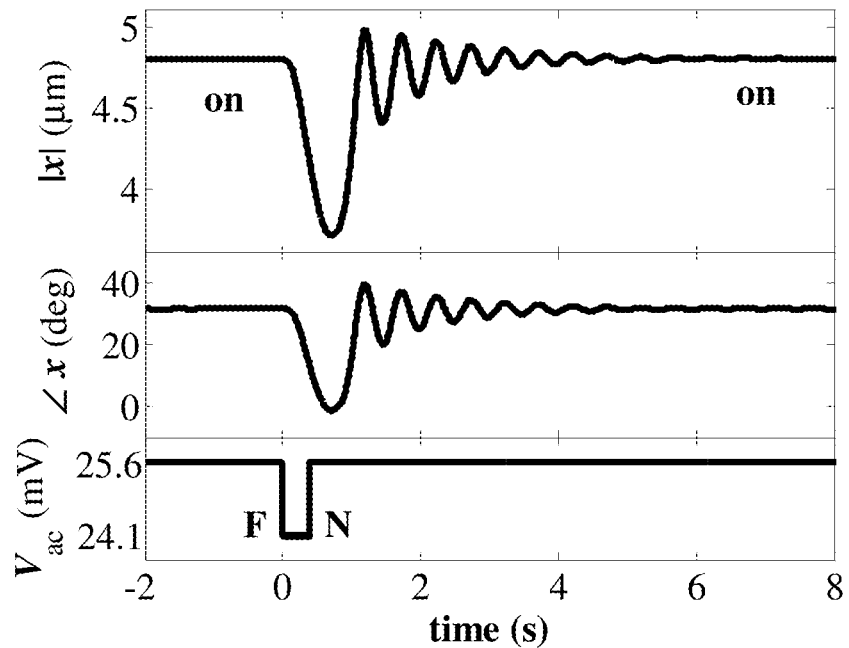
FIG. 8 depicts charts showing the recapture of the Duffing resonance by rapidly switching back to the "on" state.
Figure 9:
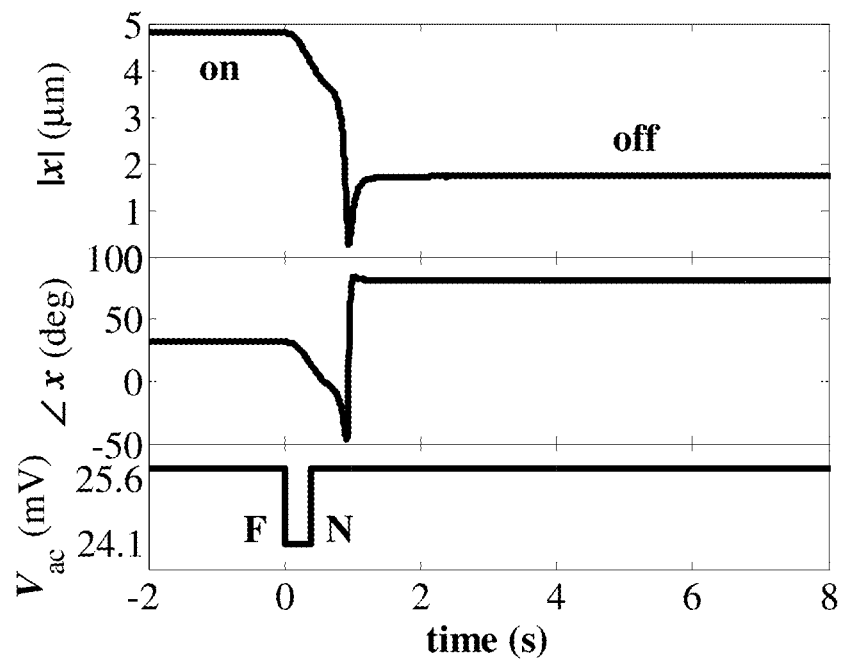
FIG. 9 depicts charts illustrating the turn-off of the Duffing resonance by increasing the off-state time beyond the critical off-state time.

Similar to the "recapture" dynamics in FIG. 12, in both FIGS. 8-9 prior to t=0 (point F), the system operates at its maximum "on" state. After point F, the resonator 100 starts to turn off and provides the initial condition for later step turn-on (point N). At point N, the system exhibits a step response due to the step turn-on in the drive amplitude $V_{ac}$. Depending on the length of the "off-state" time (the time between points F and N), the system can either recover from the decreased amplitude (FIG. 8) or completely turns off (FIG. 9). The bi-state control signal must operate at a rate much higher than the critical off-state time to avoid the ringing. The recapture dynamics in FIG. 8 gauge the "slow time" (i.e., time scale that is much longer than the resonance period) behavior of the Duffing resonator 100 and thus provide the root-locus information for later optimization of the PID 306 coefficients. In FIG. 8, the critical off-state time is 394.6 ms. In FIG. 9, the turn-off time is 395.0 ms.

Figure 15:
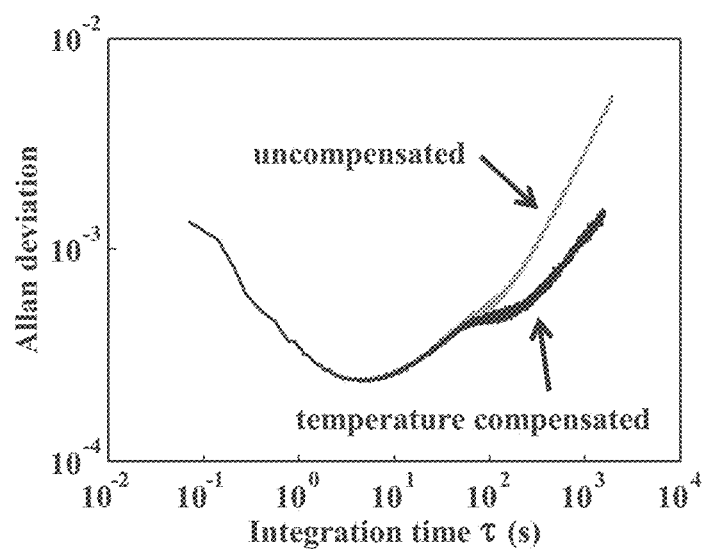
FIG. 15 represents an Allan deviation plot of the temperature compensated controller duty cycle output quantifying the stability of a particular embodiment.

Allan standard deviation of the controller 301 duty cycle output for a parametric resonator 100 is shown in FIG. 15 that represents the servo point 500 variation versus the integration time, $\tau$, and demonstrates the stability of the controller 301. The duty cycle signal is temperature compensated to eliminate the effect of temperature on the bifurcation frequency variation and hence the servo setpoint 500. As an example, the data shown in FIG. 15 represent a test performed in a constant vacuum of 18 mTorr. In this particular example, the minimum detectable duty cycle found at an integration time of 4.3 s is $2.36 \times 10^{-4}$, which corresponds to 4.48 Å resolution in displacement amplitude |x|. The low-pass filter 307 attenuates high frequency noise beyond a bandwidth of 1.95 Hz above and below the mechanical resonance at $\omega_r$=6910.7 Hz. Calibrating the gain from the duty cycle to the minimum detectable mass variation enables use of the system for a sensitive gravimetric sensor. The large displacement (1.9 μm) operation yields a much higher ratio of operation amplitude to the minimum detectable signal compared with recent bifurcation-based control schemes.

The embodiments and examples described herein demonstrate a nonlinear control of parametric and Duffing resonators 100 using a bi-state switching methodology, and further builds an ultra-sensitive platform for detecting parametric parameter changes that are indicative of resonance frequency shifts. The advantage of the system and method of the present invention is its design allowing for on-chip or off-chip implementation, and its ability to servo at relatively large amplitude (roughly four orders of magnitude larger in the displacement amplitude) along the sharp jump of the bifurcation without altering the plant. This bi-state closed-loop control system can be used in any application where mechanical resonant sensors are used now. Other types of nonlinear MEMS, nanomechanical, piezoelectric, and electrothermal devices that operate in resonance and experience bifurcation phenomena would benefit from the discrete-state control approach. The method described herein is adaptable for building robust sensor technologies including but not limited to, bifurcation-based gravimetric (mass) or chemical sensors. The most common application of the latter is in humidity sensing, widely used and commercialized on the market. This invention can also lead to the monolithic-chip implementation of the control electronics with the on-chip MEMS parametric resonator 100 to make a single-chip sensor suite.

While the system and method have been described in detail and with reference to specific embodiments and examples thereof, it will be apparent to one skilled in the art that various changes and modifications can be made therein without departing from the spirit and scope of the embodiments. Thus, it is intended that the present disclosure cover the modifications and variations of this disclosure provided they come within the scope of the appended claims and their equivalents.

What is claimed is:

1. A system for controlling a nonlinear resonator at a bifurcation frequency, comprising:
    a nonlinear resonator;
    a control loop coupled to the resonator, comprising:
        a feedback circuit for generating a feedback signal based on the output voltage of the resonator;
        an error circuit coupled to the feedback circuit, wherein the error circuit generates an error signal based on a differential between the feedback signal and a threshold value;
        a proportional-integral-derivative controller coupled to the error circuit, wherein the proportional-integral-derivative controller generates a control signal based on the error signal;
        a pulse-width modulator coupled to the proportional-integral-derivative controller, wherein the pulse-width modulator generates a bi-state control signal based on the control signal and a preset clock speed by switching between a first voltage and a second voltage;
    a drive circuit coupled to the control loop and the resonator, wherein the drive circuit receives the bi-state control signal, wherein the drive circuit generates a drive signal for the resonator based on the bi-state control signal and a reference value,
        wherein the drive signal switches the resonator between an 'on' state having a non-zero amplitude and an 'off' state having a substantially zero amplitude.

2. The system of claim 1, wherein the resonator is a parametric resonator.

3. The system of claim 1, wherein the resonator is a Duffing resonator.

4. The system of claim 1, wherein the reference value is based on a resonance frequency of the resonator.

5. A system for switching a nonlinear resonator between states at a bifurcation frequency, comprising:
    a nonlinear resonator comprising:
        a mass;
        a spring suspension;
        a first set of capacitive comb fingers interdigitated with a first set of corresponding comb fingers on the mass;
        a second set of capacitive comb fingers interdigitated with a second set of corresponding comb fingers on the mass;
        wherein the first set of capacitive comb fingers drives an effective spring constant of the resonator based on a drive voltage applied across the first set of capacitive comb fingers and the first set of corresponding comb fingers;
        wherein the second set of capacitive comb fingers produces an output signal; and
    a control loop that generates a bi-state control signal by switching between a first voltage and a second voltage, wherein the bi-state control signal switches the resonator between an 'on' state and a 'off' state in relation to a servo amplitude point at a bifurcation frequency, wherein the 'on' state has a non-zero amplitude and the 'off' state has a substantially zero amplitude.

6. The system of claim 5, wherein the control loop comprises:
    a transimpedance amplifier for receiving the output signal and generating a modified output signal;
    a lock-in amplifier, wherein the lock-in amplifier processes the modified output signal to determine the resonator velocity amplitude;
    an error circuit that compares the velocity amplitude to a threshold value, generating an error signal;
    a proportional-integral-derivative controller which receives the error signal and creates an adjusted drive signal;

a pulse width modulator that receives the adjusted drive signal and generates the bi-state control signal.

7. The system of claim 5, wherein the bi-state control signal is a square wave-form signal alternating between the first voltage and the second voltage.

8. The system of claim 5, wherein the drive voltage is a combined AC voltage and DC voltage at the parametric resonance frequency.

9. The system of claim 5, wherein the effective spring constant is a linear constant.

10. The system of claim 5, wherein the effective spring constant is a nonlinear constant.

11. The system of claim 5, wherein the bi-state control signal is a DC voltage, wherein the DC voltage is impressed across the first set of capacitive comb fingers.

12. The system of claim 11, wherein the DC voltage is at least one discrete value.

13. The system of claim 5, wherein the bi-state control signal is comprised of two discrete DC voltage values.

14. The system of claim 5, further comprising a parametric drive circuit, wherein the parametric drive circuit impresses an AC voltage across the first set of capacitive comb fingers.

15. The system of claim 14, wherein the AC voltage has a fixed frequency.

16. A method of controlling a nonlinear resonator at a bifurcation frequency having a control loop comprised of a proportional-integral-differential controller and a pulse-width modulator, the method comprising:
sensing a differential output current from the nonlinear resonator;
using the control loop coupled to the nonlinear resonator:
generating a feedback signal;
extracting a displacement signal and a phase signal based on the differential output current;
subtracting the displacement signal and the phase signal with a preset threshold value to create an error signal;
inputting the error signal into the proportional-integral-differential controller;
generating a control signal with the proportional-integral-differential controller based on the error signal;
inputting the control signal into the pulse-width modulator; and
generating a bi-state control signal by switching between a first voltage and a second voltage;
using a drive circuit coupled to the control loop and the nonlinear resonator:
using the bi-state control signal to modulate an ac drive signal, wherein the ac drive signal is integer multiple of the resonance frequency of the resonator; and
generating an electrical drive signal to the resonator based on the summation of the bi-state control signal and the ac drive signal;
wherein the electrical drive signal switches the resonator between an 'on' state having a non-zero amplitude and an 'off' state having a substantially zero amplitude.

17. The method of claim 16, wherein generating a feedback signal further comprises:
combining the differential output current with a generated signal, wherein the generated signal has a frequency equal to an integer multiple of a resonance frequency of the resonator.

18. The method of claim 16, wherein the control signal includes duty cycle information.

* * * * *